United States Patent
Boggess

(10) Patent No.: US 7,810,381 B2
(45) Date of Patent: Oct. 12, 2010

(54) HYDROSTATICALLY COMPENSATED DEEP SEA PROBE WITH SHEAR STRAIN GAUGES

(75) Inventor: Ronald Boggess, Livingston, TX (US)

(73) Assignee: Gregg Drilling & Testing, Inc., Signal Hill, CA (US)

( * ) Notice: Subject to any disclaimer, the term of this patent is extended or adjusted under 35 U.S.C. 154(b) by 322 days.

(21) Appl. No.: 12/137,376

(22) Filed: Jun. 11, 2008

(65) Prior Publication Data

US 2009/0308143 A1 Dec. 17, 2009

(51) Int. Cl.
*G01N 33/24* (2006.01)
*G01N 3/00* (2006.01)
(52) U.S. Cl. .............. 73/84; 73/85; 73/431; 73/866.5
(58) Field of Classification Search .............. 73/84, 73/85, 152.02, 152.05, 431, 862.41, 862.45, 73/866.5
See application file for complete search history.

(56) References Cited

U.S. PATENT DOCUMENTS

| | | | |
|---|---|---|---|
| 3,298,222 A | 1/1967 | Costello et al. | |
| 3,337,843 A | 8/1967 | Kendig et al. | |
| 3,455,151 A | 7/1969 | Richard | |
| 4,398,414 A * | 8/1983 | MacGregor | 73/84 |
| 4,453,401 A * | 6/1984 | Sidey | 73/73 |
| 5,125,266 A | 6/1992 | Ingram et al. | |
| 5,127,261 A | 7/1992 | Ingram et al. | |
| 5,319,959 A * | 6/1994 | Cooper et al. | 73/84 |
| 5,339,679 A | 8/1994 | Ingram et al. | |
| 5,402,165 A * | 3/1995 | Linville et al. | 348/85 |
| 5,439,800 A * | 8/1995 | Thompson | 435/9 |
| 5,493,895 A | 2/1996 | Cyr et al. | |
| 5,681,982 A | 10/1997 | Stoll et al. | |
| 5,902,939 A * | 5/1999 | Ballard et al. | 73/863.12 |
| 5,921,328 A * | 7/1999 | Babineau et al. | 175/20 |
| 6,208,940 B1 | 3/2001 | Kram et al. | |
| 6,230,820 B1 * | 5/2001 | Cordry | 175/20 |
| 6,236,941 B1 * | 5/2001 | Kram et al. | 702/12 |
| 6,317,694 B1 * | 11/2001 | Kram et al. | 702/11 |
| 6,644,423 B2 * | 11/2003 | Bratton et al. | 175/58 |
| 6,820,701 B1 * | 11/2004 | Clark et al. | 175/49 |
| 7,040,146 B2 | 5/2006 | Mackenzie et al. | |
| 7,311,011 B2 * | 12/2007 | Clark et al. | 73/864.74 |
| 2004/0118199 A1 | 6/2004 | Frost et al. | |
| 2005/0177309 A1 * | 8/2005 | Sri Ranjan et al. | 702/2 |
| 2006/0107772 A1 * | 5/2006 | Shinn et al. | 73/864.43 |

OTHER PUBLICATIONS

"Cone Testing Penetration Procedure (CPT)", Gregg Drilling, 2009.*

(Continued)

*Primary Examiner*—David A. Rogers
(74) *Attorney, Agent, or Firm*—Fulwider Patton LLP

(57) ABSTRACT

A hydrostatically compensated soil resistance probe includes a cylindrical body having a distal tip for insertion into a material, a plurality of load gates for transitioning an axial load on said cylindrical body to a shear load, and a plurality of shear load sensors to measure a transverse loading on said probe due to an axial loading. The axial loading can be the result of the resistance on the probe tip to the insertion of the probe in the soil, or the frictional forces acting on a friction sleeve as the probe passes through the soil.

15 Claims, 5 Drawing Sheets

OTHER PUBLICATIONS

J.J. Brouwer, "In Situ Soil Testing", Jan. 2007.*
"Guide to Cone Penetration Testing", Gregg Drilling, Jul. 2006.*
Robertson et al., "Interpretation of Cone Penetration Tests", Canadian Geotechnical Journal, vol. 20, No. 4, Nov. 1983.*
Sakurai et al., Reduction of Calculation Time for Load Path U Analysis of Structures, Journal of Solid Mechanics and Materials Engineering [online], Nov. 11, 2007 [rerieved on Oct. 11, 2008], Retrieved from the Internet: <URL:http://www.jstage.jst.go.jp/article/jmmp/1/11/1322/_pdf>; Fig 2; p. 1324, para 4-6.
International Search Report issued Oct. 16, 2008, pp. 1-2.

* cited by examiner

HYDROSTATICALLY COMPENSATED DEEP SEA PROBE WITH SHEAR STRAIN GAUGES

BACKGROUND OF THE INVENTION

Recent developments in deep sea exploration technology have expanded the ability to investigate ocean floors and deep sea beds as part of the initial phase of the construction of large marine production facilities and pipelines. Examination of the ocean bed's surface is important in evaluating locations for foundations that will anchor platforms for such things as deep sea oil exploration and production rigs and other structures for mining of the ocean floor. For example, the rise in oil prices world wide has led to the investigation of large scale oil drilling platforms in deeper waters such as the Gulf of Mexico, off the coast of South America, Africa and China. Determining the physical and mechanical properties of the soil is critical for evaluating possible foundation locations (along with currents and other local conditions), and thus physical testing of the ocean floor in deep oceanic waters is of vital importance. The high cost of these structures dictates very precise measurements of the soil conditions, which can be in waters several thousands of meters deep. The most common type of testing performed in these conditions is in situ examination of the mechanical response of the soil using a probe such as a cone penetration test (CPT). Cone penetration tests are widely used for an extensive range of applications from terrestrial soil to shallow marine soil to deep sea soil. A brief description of a typical CPT probe and test can be found at http://www.conepenetration.com/online-book/cf-cone/cf-cone-cone-penetration-test/.

The cone penetration test involves a cone tip and cylindrical body that is forced into the soil at a constant rate. A sensor is coupled to the cone tip to measure the strength of the soil, and the cylindrical body is typically equipped with a sleeve to measure the shear forces on the probe as it slides into and through the soil. While the probe penetrates the soil, continuous measurements are taken of the resistance to the cone's penetration and the frictional forces acting on the surface of the sleeve. Stress gauges located in the cavity of the probe measure the compressive force on the cone due to the resistance of the soil as well as the frictional forces on the outer surface. Cables or wires located in the cavity transmit signals to the surface or recording device where they can be analyzed. The use of cone penetration tests, and piezocone test data, are well known in the art for measuring sub-surface conditions of soil both on land and at sea, and for purposes of brevity a more detailed explanation of the structure and techniques of cone penetration testing is omitted herein.

One problem that is fairly unique to the process of deep sea testing concerns the high pressure that is present in that environment and its effect on the precision of the measurements of the soil strength. Cone penetrometers utilize a Wheatstone bridge type stress gauge to measure the stress on the cone tip due to its contact with the surface it is measuring. However, the large pressures on the cone's exterior due to the hydrostatic pressure from hundreds or even thousands of cubic meters of seawater compress the cone and result in detected loads much greater than those caused by the soft deep sediments. When the measurements occur at depths over a thousand meters, the hydrostatic pressure can dominate the stresses that are the subject of the testing, namely the insertion of the cone into the often soft soil at the ocean floor.

To mitigate the external hydrostatic pressure on the probe, it is known in the art to internally pressurize the probe with a non-conducting fluid such as an oil to balance the probe's internal pressure with the external pressure. The internal pressure can be linked to the external pressure so as to maintain equilibrium in the probe during its decent and at the location of the testing. By filling the internal cavity of the probe with a non-conductive oil the external hydrostatic pressure can be balanced. However, this pressure balancing of the probe creates a Poisson's effect where a longitudinal strain and transverse strain in the load cell are unequal. This longitudinal strain is in the same direction as the compression measured by the probe's contact with the ocean bed, and proportional to the pressurization. Therefore, this introduced stain is many times greater than the strain to be measured.

This Poisson's effect leads to a condition where the strain gauges must be zeroed out prior to the test, or somehow compensated to eliminate this artificial strain that is due to the hydrostatic pressure, prior to measuring the actual strain on the probe due to the resistance of the soil to be measured. Zeroing out the gauges is not an optimum solution, however, because the accuracy of the strain gauges are a function of the maximum load, typically around ±0.1% of the maximum load. In the case of Wheatstone bridge type stain gauges, the maximum load is on the order of 40,000-50,000 KPa corresponding to the hydrostatic pressure, whereas the pressure due to the sea bed soil insertion may be only 10-20 KPa. Accordingly, when dealing with soft soils, the error due to the zeroing can be great compared with the actual measurement of the soil, significantly limiting the precision of the results. The foundational design for deep sea structures is dependent upon the results of such testing, and the cost of these structures dictate that precise soil strength measurements are critical to the success of such multi-million dollar projects. Accordingly, there is an urgent and unfulfilled need to improve the quality and precision of deep sea testing of ocean beds that does not subject the gauges to the enormous hydrostatic pressures that are inherent in in situ testing.

SUMMARY OF THE INVENTION

A hydrostatically equilibrated probe includes a load cell with a plurality of elongate circumferentially extending cavities that create load gates at two axial locations on the load cell. By arranging the load gates so that they are circumferentially offset, axial loads must be carried diagonally in the load cell and are transformed into shear loads. Shear loads are not affected by the Poisson's effect of the internal pressurization, and so the shear gauges placed adjacent the load gates measure only the forces due to the resistance of the soil. Because the output of the shear gauges is unaffected by the hydrostatic pressure, they can be selected judiciously such that the maximum loading is very close to the anticipated loading of the soil resistance forces, and accuracy is improved by an order of magnitude or more over existing load cells that must account for the hydrostatic pressure.

Other features and advantages of the invention will become apparent from the following detailed description, taken in conjunction with the accompanying drawings which illustrate, by way of example, the features of the invention

DETAILED DESCRIPTION OF THE PREFERRED EMBODIMENTS

Figure 1:
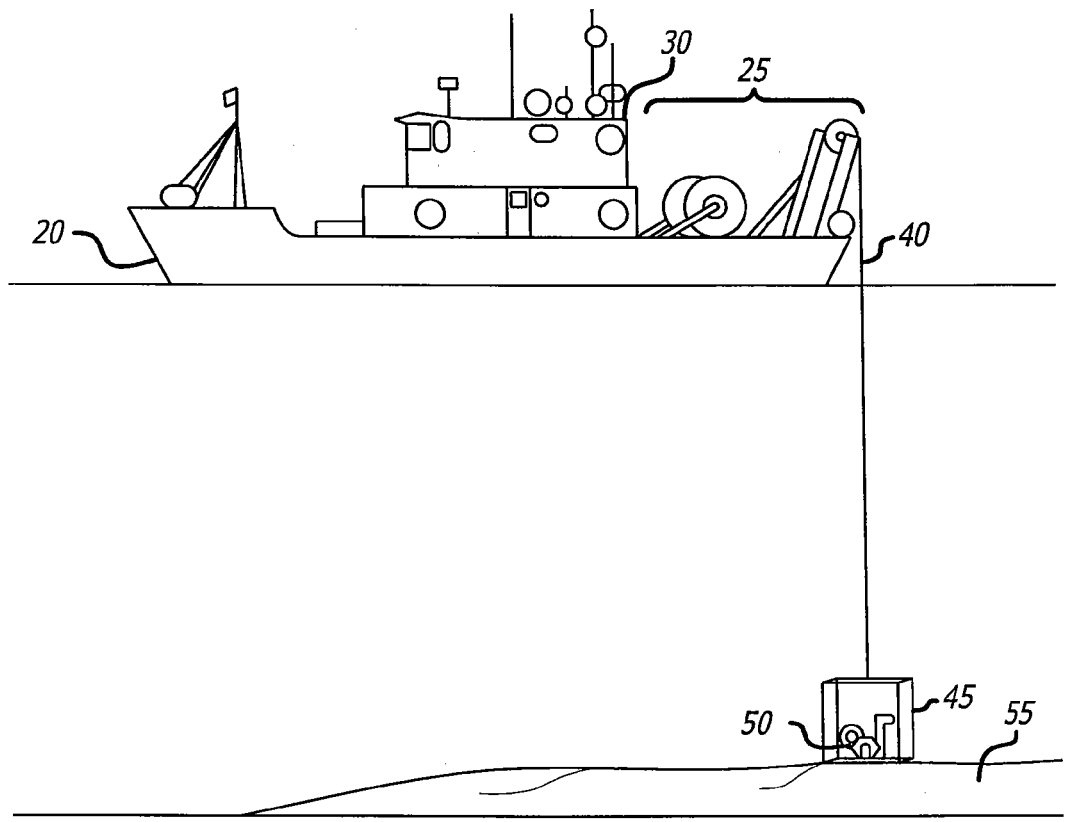
FIG. 1 is a perspective view of the environment for which the present invention is developed.

FIG. 1 depicts a self-propelled ocean going vessel 20 such as might be used to conduct deep sea experiments on the ocean floor, including a winch 25 and global positioning equipment 30 for precisely locating the ship. An umbilical cable 40 communicates electronic signals to and from a drilling cage 45. The cage 45 includes a thrusting unit 50 that pushes the probe into the soil 55 when commanded by the control unit aboard the ship 20. In practice, the vessel's winch 25 lowers the cage to the ocean floor and the G.P.S. equipment measures the precise location of the ship. The control unit then commands the thrusting unit 50 to force the probe downward into the soil at a constant rate, and measurements are taken at constant intervals (for example, every five centimeters) to evaluate the conditions of the soil at the selected location. The measurements are communicated as electronic signals to a computer aboard the vessel 20 that converts the signals to numerical data from which the user can interpret the forces on the probe due to the insertion into the soil. ASTM standard D 5778-95 governs cone penetration test soundings.

Figure 2:
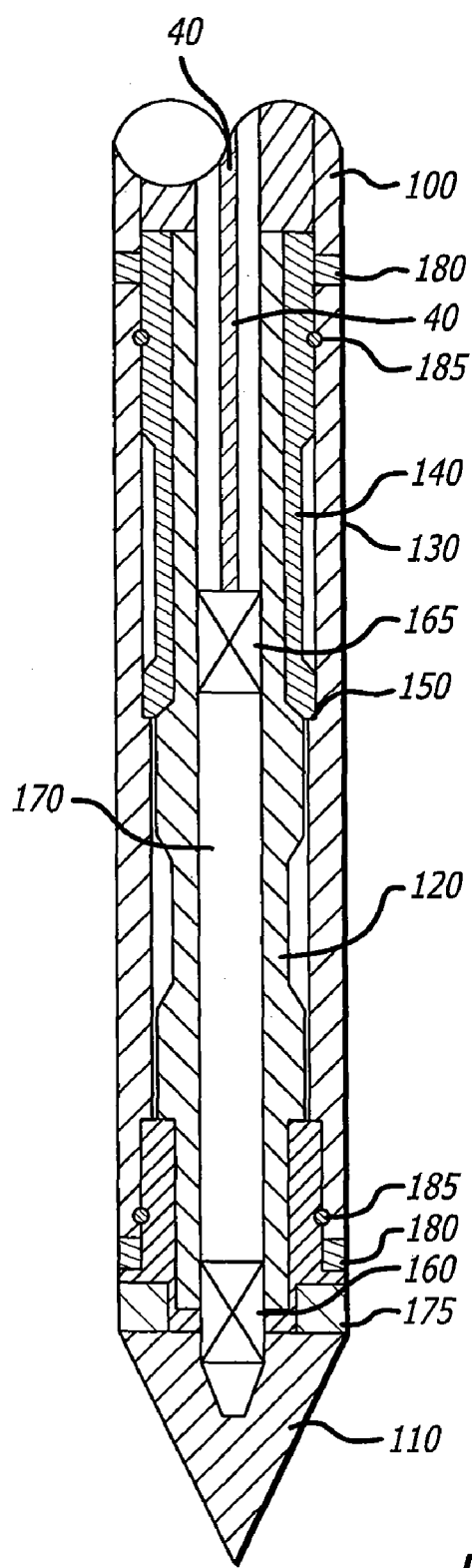
FIG. 2 is a cross sectional view of a cone penetration test probe as utilized by the present invention.

FIG. 2 illustrates a cross sectional view of the probe 100 utilizing the present invention. The probe is formed of a cone tip 110, a tip load cell 120, a friction sleeve 130, and a friction load cell 140. The cone tip 110 can have a 60° apex angle and can have a projected area $A_c$ of, for example, 2 cm$^2$, 10 cm$^2$, and 15 cm$^2$, depending upon the diameter of the probe. The cone may be made of metal such as aluminum, steel or titanium and has a capacity consistent with the expected loads. The total force acting on the cone, $Q_c$, divided by the projected area of the cone, $A_c$, produces the cone resistance, $q_c$. The force acting on the surface of the cone tip 110 is transferred to the tip load cell 120, which measures the soil's resistance. Similarly, the total force acting on the friction sleeve 130, $F_s$, divided by the surface area of the frictional sleeve 130, $A_s$, produces the sleeve friction, $f_s$. The friction sleeve 130 is coupled to the friction load cell 140 at an inner shoulder 150 such that a force on the friction sleeve 130 is transferred to the friction load cell 140.

A pore pressure transducer 160 measures the water pressure on the outside of the cone and relays that information to the surface via the cable 40. An inclinometer 165 can be secured inside the cavity 170 of the tip load cell 120 and relays information on the angle of penetration of the probe 100 compared to vertical. In the exemplary embodiment, probe is equipped with a porous filter 175 made of plastic and approximately 5 millimeters thick. The filter 175 is used to obtain penetration pore pressure as the cone is advanced as well as pore pressure dissipation during any pauses in the penetration. Soil seals 180 prevent soil from entering the probe and contaminating the instruments, and water seals 185 prevent water from entering the probe and interfering with the pressurization of the probe 100. All of the data is transferred via an electronic cable 40 traveling up the probe's internal cavity 170 or stored in RAM. CPT data reduction and interpretation may therefore be performed in real time facilitating on-site decision making.

Figure 3:
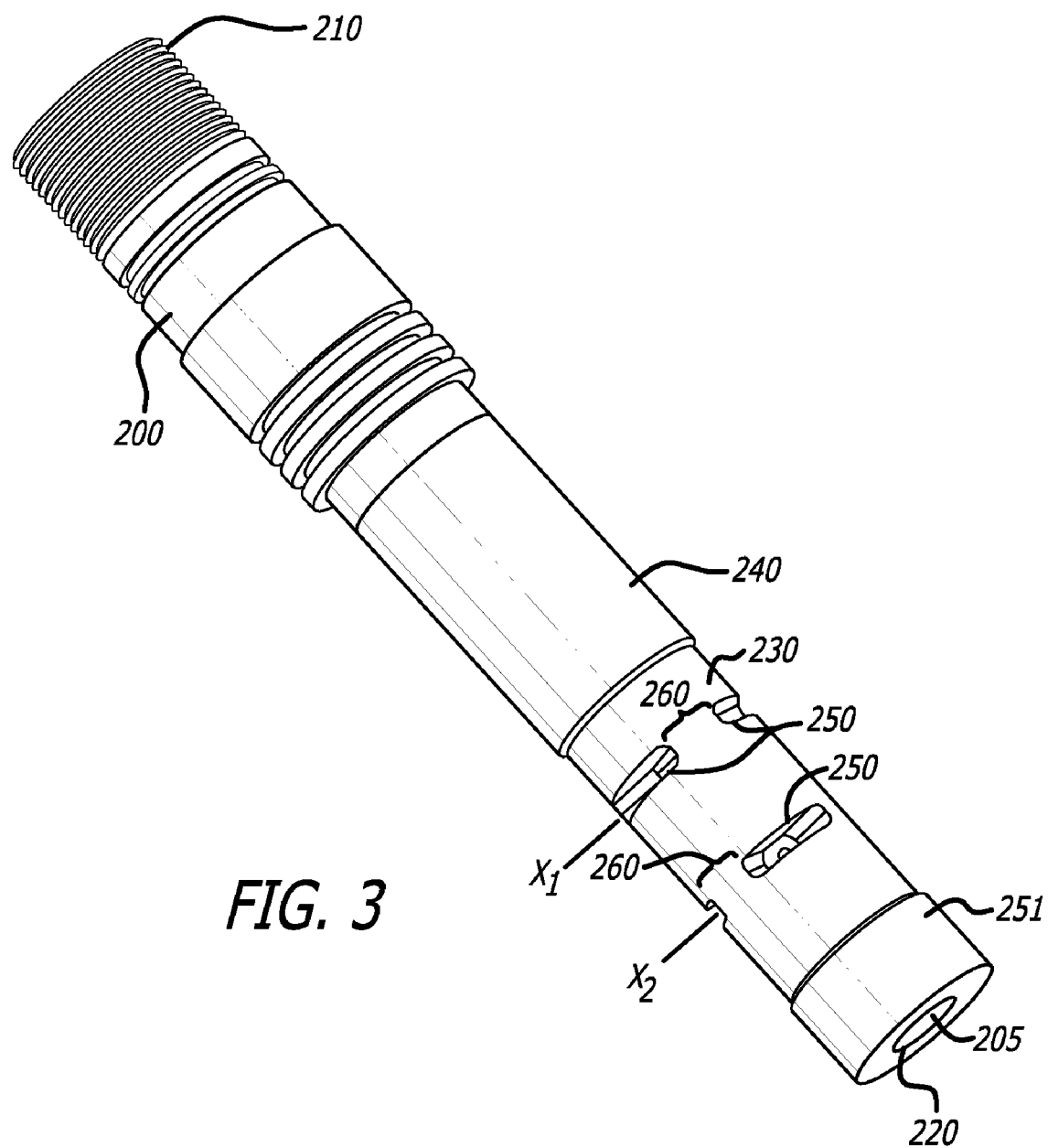
FIG. 3 is an enlarged, elevated perspective view of the load cell of the present invention.
Figure 4:
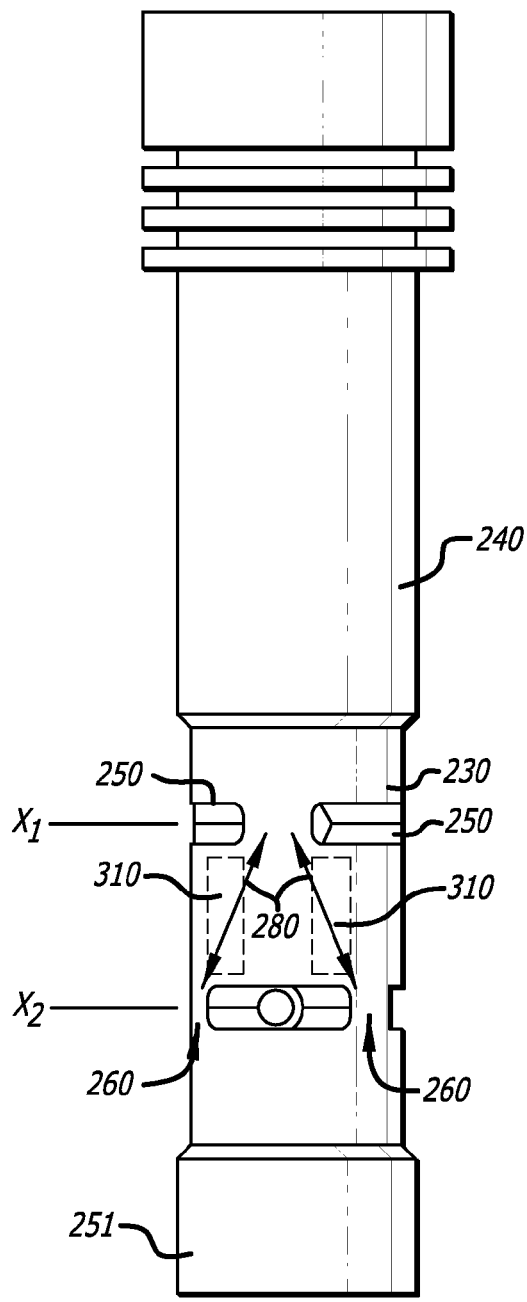
FIG. 4 is an enlarged, sectional view of the load cell of the present invention.

The load cell of the present invention is depicted in FIG. 3, which shows an elongate hollow tube 200 configured with a tubular wall defining an axial channel 205. The tube 200 has an externally threaded first end 210 and an internally threaded second end 220. The tube 200 is formed medially with a radially stepped-down section to define a recessed portion 230 having a slightly smaller outer radius than the adjacent upper and lower end sections 240, 251 of the tube. At two spaced apart axial positions $x_1$ and $x_2$, elongate circumferentially extending holes 250 define circumferential slots that are disposed in the recessed portion 230 of the cell 200 to form load gates 260 between each pair of circumferentially spaced slots 250. The slots 250 at the first position $x_1$ are conveniently arranged so that they are axially aligned with the load gates 260 of the second position $x_2$, and vice versa. That is, the load gates at the first axial position are angularly offset from the load gates at the second axial position. As a result of this angular offset of the load gates 260, forces must travel in a diagonal spiraling path (shown in FIG. 4 as diagonal lines 280) from any load gate 260 at the first position $x_1$ to a load gate at a second position $x_2$. In this recessed portion 230, therefore, purely axial loads are converted to shear loads due to the presence of the slots 250 as the forces propagate diagonally from position one $x_1$ to position two $x_2$ on the load cell tube. As will be appreciated by those skilled in the art, the holes 250 serve as weakened areas in the wall of the tube 200 to form the respective load gates 260. The holes may take many different forms and shapes and may in fact be merely weakened segments in the tube wall.

Figure 5:
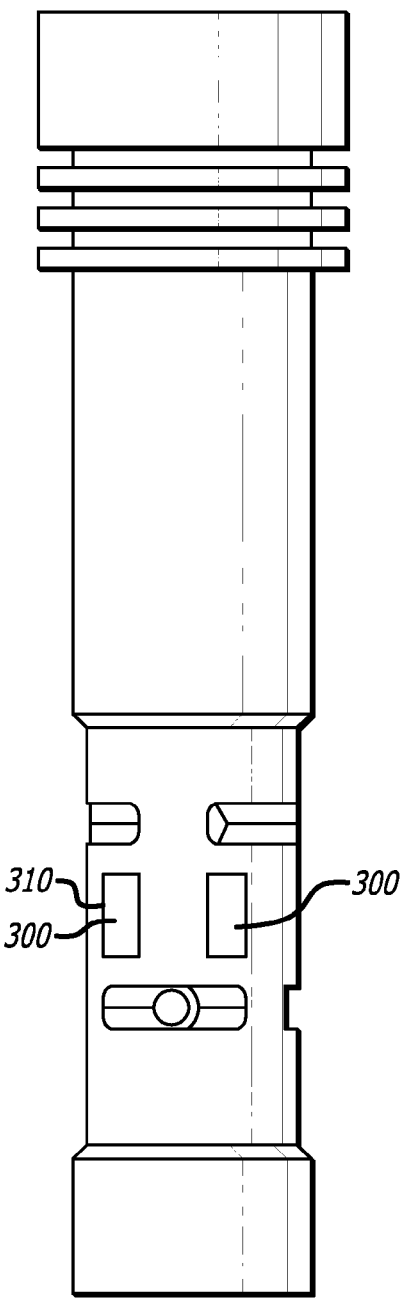
FIG. 5 is an enlarged, sectional view of the load cell showing the position of the shear strain gauges.

To measure the shear strain in the load cell 200, in the preferred embodiment shear strain gauges 300 are located on each load cell (the tip load cell and the friction load cell), each at an axial and lateral area of overlap 310 in the respective areas between hole 250 at position one $x_1$ and a hole 250 at position two $x_2$ as shown in FIG. 5. All of the axial or frictional load passing through the load cell 200 must pass across the composite areas of overlap 310 where the shear strain gauges 300 are located as the forces propagates up the load cell between the load gates 260, and the gauges 300 measure the shear load and generate a corresponding electrical signal that can be converted by the vessel's onboard computer to an equivalent axial load. The load cell of the present invention can be coupled to a cone tip 110 and used as a tip load cell for measuring the tip load, or coupled to a friction sleeve 130 and used as a friction load cell for measure the frictional loading. In a preferred embodiment, a cone penetration test probe will include both a tip load cell and a friction load cell using the improved load cells with shear strain gauges as described above.

Figure 6:
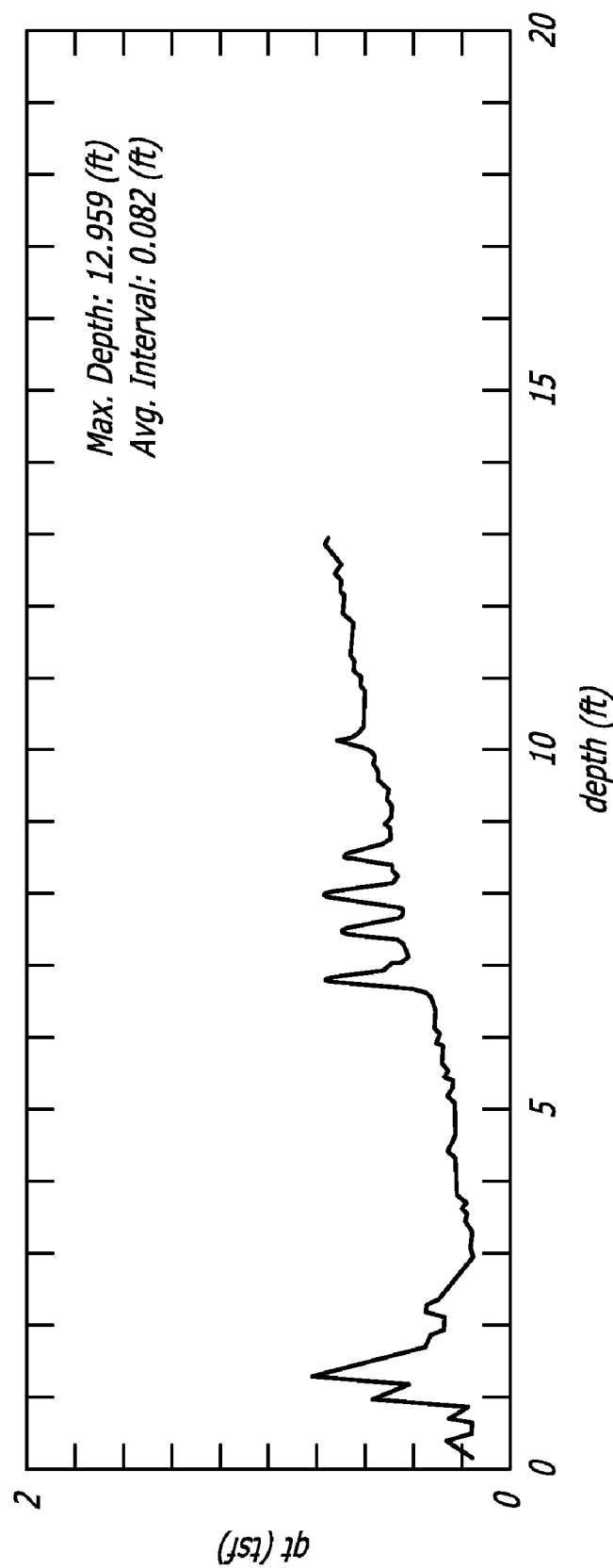
FIG. 6 is a graph showing a plot of $q_t$ versus depth using a load cell of the present invention.

The use of shear strain gauges eliminates the Poisson's effect due to the pressurization of the load cell to offset the hydrostatic pressure, so the strain gauges can be selected based on the anticipated loading due to the forces from the soil only. This is a significant advantage over present systems, and allows for measurements that are far more accurate that any measurements without this invention. FIG. 6 shows a graph of cone resistance $q_t$ versus depth of cone penetration at a water depth of over one thousand meters. At this depth, the hydrostatic pressure is well over 1 MPa, but the readings on the gauge shows a maximum resistance of approximately 0.8 tsf, or about 77 kPa. Had the gauges needed to be selected based on the hydrostatic pressure of 1 MPa, the accuracy (0.1% of highest reading) would be greatly diminished as compared with the actual measured values. The improved accuracy is realized to an even greater extent in the frictional load cell, which experiences smaller overall strains than the tip load cell and thus its comparison with the hydrostatic forces is even greater. Accordingly, the present invention reflects a marked improvement over traditional systems.

The number of slots 250 is not critical to the present invention, as a load cell can have more or less as long as the position of the load gates ensure that the axial loads are converted into shear loads at the positions of overlap 310 where the shear strain gauges 300 are located. The load gates must be strong enough to satisfy the loading condition without buckling or deforming, so some structural limitations may influence the number of holes 250. Each load cell can include 12 strain gauges, where each Wheatstone bridge has four arms and there are three strain gauges for each arm. Each load cell as six load gates (for the three hole configuration), and each gate has two strain gauges. Other configurations using more or less gauges are within the knowledge of those of ordinary skill in the art.

The description above is intended to be illustrative of the present invention without limiting the present invention to the embodiments described herein. For example, one of ordinary skill in the art would recognize various modifications to the above described embodiments, such as geometries, sizes, interaction between the load cells and the cone tip or frictional sleeve, and so forth. Accordingly, it should be understood that the scope of the present invention is properly measured by the appended claims, using definitions of claim terms according to their plain and ordinary meaning and without limitation to any specific disclosure in the specification.

I claim:

1. A hydrostatically compensated soil resistance probe comprising:
    an elongated tubular body having a distal tip for insertion into a material;
    a first load gate laterally arrayed around the tubular body at a first axial position, and a second load gate angularly offset from said first load gate at a second axial position, said first and second load gates configured to, upon application of an axial force to said tubular body, redirect said axial force to a shear force;
    a shear sensor on said tubular body between said first and second load gates to measure said shear force; and
    a sleeve member enclosing the shear sensor and the first and second load gates.

2. The hydrostatically compensated soil resistance probe of claim 1 wherein said body includes a conical tip.

3. The hydrostatically compensated soil resistance probe of claim 1 wherein said tubular body is formed with circumferential, spaced apart openings cooperating to define therebetween the respective load gates.

4. The hydrostatically compensated soil resistance probe of claim 3 wherein said holes of the respective said first and second load gates are spaced and configured so as to form therebetween laterally overlapping stress sections.

5. The hydrostatically compensated soil resistance probe of claim 1 comprising three load gates at said first axial position and three load gates at said second axial position.

6. The hydrostatically compensated soil resistance probe of claim 1 that includes two shear sensors for each load gate.

7. The hydrostatically compensated soil resistance probe of claim 1 wherein the shear sensors are selected independent of an applied hydrostatic pressure.

8. The hydrostatically compensated soil resistance probe of claim 1 wherein the tubular body is cylindrical.

9. The hydrostatically compensated soil resistance probe of claim 1 for use in deep sea explorations and includes a push rods connected to said tubular body.

10. The hydrostatically compensated soil resistance probe of claim 1 for use with a sea going vessel having an on-board computer and that includes means responsive to said shear force to generate corresponding electrical signals and means for communicating said electrical signals to said computer.

11. A hydrostatically compensated soil resistance probe for testing soil and comprising:
    an elongated probe body portion having an upper end and a lower end;
    a conical probe tip attached to the lower end of the probe body to be driven into said soil by an axial force;
    means for redirecting said axial force on said probe body portion to a shear loading;
    a sensor for measuring said shear loading; and
    a sleeve member enclosing said redirecting means and said sensor.

12. A method for measuring the axial load on a hydrostatically compensated soil probe comprising:
    providing a probe having a tubular body and tapered tip;
    filling the probe with a non-conducting fluid at a pressure to match an external pressure on said probe;
    providing a load cell within said tubular body and immersed in said fluid, said load cell coupled to said conical tip to transfer a resistance of said soil to said load cell, said load cell configured with load gates at first and second axial positions, said load gates at said first axial position angularly offset from said load gates at said second axial position;
    configuring the load cell with shear sensors to measure a shear force on said load cell due to the resistance of said soil;
    providing a sleeve member enclosing the shear sensors and the load gates;
    driving the probe into the soil at a substantially constant rate;
    communicating signals from said shear sensors on said load cell to a computer; and
    converting the signals from said load cell to an axial load resulting from said resistance of the probe to said soil.

13. The method of claim 12 wherein the said tubular body is cylindrical.

14. The method for measuring the axial load on a hydrostatically compensated soil probe of claim 12 further comprising:
    providing a second load cell within said tubular body and immersed in said fluid, said second load cell coupled to a frictional sleeve on said conical body to transfer a resistance of said soil to said second load cell, said second load cell configured with load gates at first and second axial positions, said load gates at said first axial position angularly offset from said load gates at said second axial position;
    configuring the second load cell with shear sensors to measure a shear force on said load cell due to the resistance of said soil;
    communicating signals from said shear sensors on said second load cell to a computer; and
    converting the signals from said second load cell to a frictional load resulting from said resistance of the probe to said soil.

15. The method of claim 12 wherein said shear sensors are selected independent of an external pressure on said probe.

* * * * *